US010154945B2

(12) United States Patent
Jang et al.

(10) Patent No.: US 10,154,945 B2
(45) Date of Patent: Dec. 18, 2018

(54) SINGLE PASTE TYPE HYDRAULIC DENTAL FILLING COMPOSITION

(71) Applicant: Maruchi, Wonju-si (KR)

(72) Inventors: Sung Wook Jang, Seoul (KR); Ho Nam Lim, Seoul (KR); Eui Seong Kim, Seoul (KR); Sei Jin Oh, Gunpo-si (KR)

(73) Assignee: MARUCHI, Wonju-si, Gangwon-Do (KR)

( * ) Notice: Subject to any disclaimer, the term of this patent is extended or adjusted under 35 U.S.C. 154(b) by 247 days.

(21) Appl. No.: 15/246,836

(22) Filed: Aug. 25, 2016

(65) Prior Publication Data

US 2016/0361237 A1 Dec. 15, 2016

Related U.S. Application Data

(63) Continuation of application No. PCT/KR2015/001822, filed on Feb. 25, 2015.

(30) Foreign Application Priority Data

Feb. 25, 2014 (KR) ........................ 10-2014-0021907
Mar. 20, 2014 (KR) ........................ 10-2014-0032686

(51) Int. Cl.
| | |
|---|---|
| *A61K 6/00* | (2006.01) |
| *A61K 6/02* | (2006.01) |
| *A61K 6/06* | (2006.01) |
| *A61K 6/08* | (2006.01) |
| *C08L 1/00* | (2006.01) |
| *C08L 1/04* | (2006.01) |
| *C04B 14/30* | (2006.01) |
| *C04B 22/00* | (2006.01) |
| *C04B 24/26* | (2006.01) |
| *C04B 24/38* | (2006.01) |
| *C04B 28/02* | (2006.01) |
| *C04B 28/04* | (2006.01) |
| *C08L 29/04* | (2006.01) |
| *C08L 39/06* | (2006.01) |
| *C04B 103/00* | (2006.01) |
| *C04B 103/46* | (2006.01) |
| *C04B 111/00* | (2006.01) |

(52) U.S. Cl.
CPC .......... *A61K 6/0073* (2013.01); *A61K 6/0002* (2013.01); *A61K 6/0008* (2013.01); *A61K 6/0038* (2013.01); *A61K 6/0047* (2013.01); *A61K 6/0205* (2013.01); *A61K 6/0606* (2013.01); *A61K 6/0612* (2013.01); *A61K 6/0618* (2013.01); *A61K 6/0675* (2013.01); *A61K 6/0681* (2013.01); *A61K 6/08* (2013.01); *C04B 14/306* (2013.01); *C04B 22/0093* (2013.01); *C04B 24/2623* (2013.01); *C04B 24/2652* (2013.01); *C04B 24/383* (2013.01); *C04B 28/02* (2013.01); *C04B 28/04* (2013.01); C04B 2103/0051 (2013.01); C04B 2103/465 (2013.01); C04B 2111/00836 (2013.01)

(58) Field of Classification Search
CPC .... A61K 6/007; A61K 6/0073; A61K 6/0606; A61K 6/0618; A61K 6/06; A61K 6/0008; A61K 6/0038; A61K 6/0047; A61K 6/0675; C04B 14/306; C04B 22/062; C04B 28/02; C04B 28/04; C04B 28/021; C04B 2103/00051; C04B 2103/465; C04B 2111/00836

See application file for complete search history.

(56) References Cited

U.S. PATENT DOCUMENTS

| | | | | |
|---|---|---|---|---|
| 5,415,547 | A | * 5/1995 | Torabinejad | A61C 5/00 433/228.1 |
| 2007/0009858 | A1 | 1/2007 | Hatton et al. | |
| 2008/0299093 | A1 | * 12/2008 | Yang | A61L 24/0015 424/93.7 |
| 2011/0244431 | A1 | * 10/2011 | Shinozaki | A61K 6/0625 433/228.1 |
| 2012/0035296 | A1 | 2/2012 | Nakamura et al. | |
| 2013/0023601 | A1 | 1/2013 | Ogliari et al. | |

FOREIGN PATENT DOCUMENTS

| | | | |
|---|---|---|---|
| GB | 403230 | * | 12/1933 |
| JP | 2000351958 | A | 12/2000 |
| KR | 10-2008-0091426 | A | 10/2008 |
| KR | 20090125141 | A | 12/2009 |

* cited by examiner

*Primary Examiner* — C Melissa Koslow
(74) *Attorney, Agent, or Firm* — Dinsmore & Shohl LLP; Yongsok Choi

(57) ABSTRACT

According to one aspect of the present disclosure, there is provided a single paste type hydraulic dental filling composition. The single paste type hydraulic dental filling composition includes hydraulic cement, non-aqueous liquid having hygroscopic properties, and a radiopaque material.

14 Claims, 1 Drawing Sheet

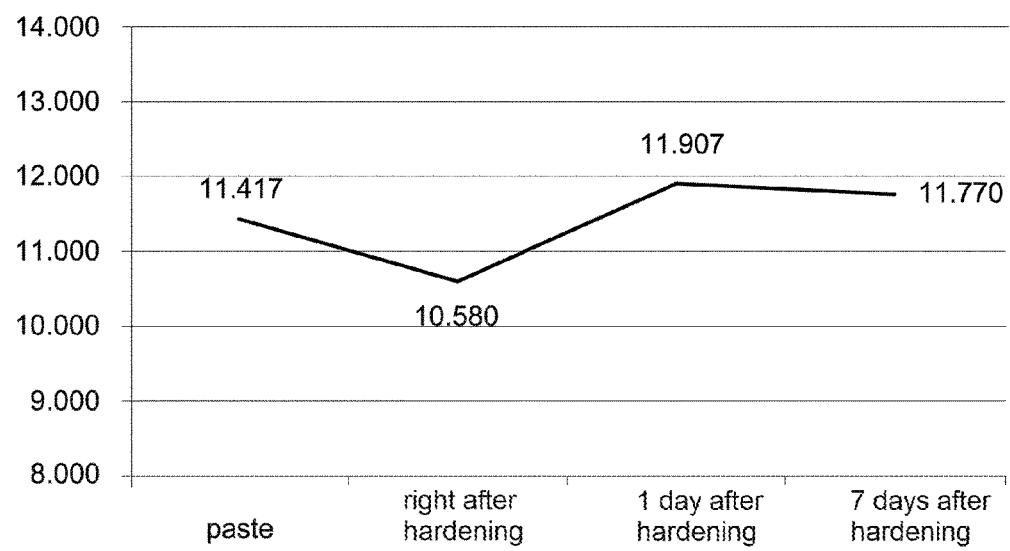

SINGLE PASTE TYPE HYDRAULIC DENTAL FILLING COMPOSITION

CROSS REFERENCE TO RELATED APPLICATIONS

This application is a continuation application of Patent Cooperation Treaty (PCT) international application Serial No. PCT/KR2015/001822, filed on Feb. 25, 2015, which designates the United States, and claims priority to Korean Patent Application Serial No. 10-2014-0021907, filed on Feb. 25, 2014 and Korean Patent Application Serial No. 10-2014-0032686, filed on Mar. 20, 2014. The entirety contents of PCT international application Serial No. PCT/KR2015/001822, Korean Patent Application Serial No. 10-2014-0021907, and Korean Patent Application Serial No. 10-2014-0032686 are incorporated herein by reference.

FIELD

The present disclosure relates to a single paste type hydraulic dental filling composition, and more particularly, to a single paste type hydraulic dental filling composition characterized by comprising hydraulic cement and non-aqueous liquid, and hardening quickly by absorbing moisture from ambient liquid or air.

BACKGROUND

Endodontics is a specific branch of dentistry related to pathological treatment of dental pulp or apical tissue.

The inner part of a tooth contains nerves and blood vessel tissues called dental pulp, which is covered by dentin, and the outermost part of the tooth contains enamel. Endodontic treatment is conducted mainly when the dental pulp is infected.

Endodontic treatment of a tooth having pulp tissue in which inflammation is in progress or necrosis has occurred is generally conducted by opening an inner space of the tooth called a pulp chamber through an access cavity formed in a crown of the tooth, and putting an endodontic instrument into a canal within a root of the tooth.

After the endodontic treatment is finished, the root canal is sealed using a root canal filler to prevent secondary infection. An ideal dental root canal filler may be excellent in properties such as biocompatibility, bactericidal properties, sealing properties, stability, workability, injectability and dispersibility, and radiopacity.

Examples of the root canal filler may include gutta percha and a sealer. Endodontic treatment employing gutta percha and a sealer may be considered as conservative treatment. This is commonly conducted by two techniques, i.e., lateral and vertical condensation techniques. In the lateral condensation technique, a gutta percha cone is put inside a root canal and laterally condensed using a spreader tool to fill the root canal, and then empty space between the filled gutta percha and the root canal is filled with a sealer. In the vertical condensation technique, gutta percha is inserted in a root canal and vertically condensed using a plugger tool to fill the root canal.

However, according to those conventional techniques, there is a risk that the root canal could be fractured or damaged in the process of applying pressure to the gutta percha. Further, a tooth has a root canal system having complicated and diverse shapes, thus requiring more secure sealing.

Meanwhile, when a general endodontic treatment process is unsuccessfully conducted or a non-surgical treatment cannot fully remove inflamed tissues due to the state or condition of the tooth, a surgical endodontic treatment is conducted to preserve the tooth. In this case, what is most frequently conducted is to cut off a root apex of the tooth (i.e., to conduct apicoectomy) and prepare a cavity for retrograde filling at the tip thereof so that an artificial material is filled. According to the above, tissues or germs existing within the infected root canal cannot be disseminated to tissues around the tooth root (i.e., tissues around the root apex) so that inflammation of the tissues around the root apex may be prevented and the tooth may be preserved for a long period.

Various materials have been employed for retrograde filling of a root apex, and biological/physical assessments thereof are being diversely conducted. The known materials that may be considered include gutta percha, polycarboxylate cement, amalgam, Super-EBA, Cavit, zinc oxide, eugenol, glass-ionomer cement, zinc phosphate cement, and the like. However, it has been reported that some of the above materials have low biocompatibility or have poor physical properties making them unsuitable for use in a surgical environment where blood or other moisture exists.

In contrast, MTA (mineral trioxide aggregate) cement is known as a material having excellent biocompatibility and sealing properties. It has become a typical dental material that may be extensively used for retrograde filling of a root apex and closing of perforation, and may be employed in procedures including pulp capping, pulpotomy, artificial apical barrier placement (apexification), revascularization and apexogenesis procedure, and the like. Therefore, since the MTA cement is hardened with water and thus has good sealing properties in a humid environment, diverse efforts are being made to employ it for root canal filling, and among those, researches on using the MTA cement made in the form of paste are being actively conducted. In this connection, one example thereof may be the technique disclosed in Korean Laid-open Patent Publication No. 10-2010-0037979.

However, although it is generally assumed that a root canal is under a humid environment, every root canal is not always in a humid state since many dentists are familiar with drying the root canal in an endodontic treatment process. Further, the existing MTA cement products have low usability since they should be mixed with liquid immediately before being injected into the root canal, and have relatively poor flowability and manipulability so that it takes a long time for them to be positioned deep inside the root canal.

Therefore, the inventor(s) present a single paste type MTA cement that absorbs ambient moisture even in a dried root canal to securely harden within an appropriate time.

SUMMARY

One object of the present disclosure is to solve all the above-described problems.

Another object of the disclosure is to provide a single paste type dental filling composition that requires no additional mixing process and can be provided as contained in a syringe.

Yet another object of the disclosure is to provide a single paste type dental filling composition that has good biocompatibility and hardens quickly so that a root canal or a perforated region of a tooth may be easily sealed in three dimensions.

Still another object of the disclosure is to provide a single paste type dental filling composition that easily hardens by absorbing moisture from wet cotton or from tissue fluid or air within or around a root canal.

Still yet another object of the disclosure is to provide a single paste type dental filling composition that requires no application of heat and pressure, thereby enhancing safety.

According to one aspect of the disclosure to achieve the above objects, there is provided a single paste type hydraulic dental filling composition, comprising: hydraulic cement; non-aqueous liquid having hygroscopic properties; and a radiopaque material.

In addition, there may be further provided other compositions according to the technical idea of the disclosure.

According to the disclosure, there is provided a single paste type dental filling composition that requires no additional mixing process and can be provided as contained in a syringe.

According to the disclosure, there is provided a single paste type dental filling composition that has good biocompatibility and hardens quickly so that a root canal or a perforated region of a tooth may be easily sealed in three dimensions.

According to the disclosure, there is provided a single paste type dental filling composition that easily hardens by absorbing moisture from wet cotton or from tissue fluid or air within or around a root canal.

According to the disclosure, there is provided a single paste type dental filling composition that requires no application of heat and pressure, thereby enhancing safety.

BRIEF DESCRIPTION OF THE DRAWINGS

FIG. 1 is a graph according to Test Example 4 of the disclosure.

DETAILED DESCRIPTION

In the following detailed description of the present disclosure, references are made to the accompanying drawings that show, by way of illustration, specific embodiments in which the disclosure may be practiced. These embodiments are described in sufficient detail to enable those skilled in the art to practice the disclosure. It is to be understood that the various embodiments of the disclosure, although different from each other, are not necessarily mutually exclusive. For example, specific shapes, structures and characteristics described herein may be implemented as modified from one embodiment to another without departing from the spirit and scope of the disclosure. Furthermore, it shall be understood that the locations or arrangements of individual elements within each of the embodiments may also be modified without departing from the spirit and scope of the disclosure. Therefore, the following detailed description is not to be taken in a limiting sense, and the scope of the disclosure is to be taken as encompassing the scope of the appended claims and all equivalents thereof. In the drawings, like reference numerals refer to the same or similar elements throughout the several views.

Hereinafter, various embodiments of the present disclosure will be described in detail with reference to the accompanying drawings to enable those skilled in the art to easily implement the disclosure.

1) Hydraulic Cement

The filling composition according to the disclosure may comprise hygroscopic hydraulic cement that hardens by absorbing moisture within or around a root canal, and has good biocompatibility and sealing properties.

The hydraulic cement may comprise calcium oxide or calcium hydroxide as an active component, and may comprise Portland cement or Pozzolan cement. Particularly, it may comprise Portland cement, which has physical properties and chemical composition similar to those of MTA and has good biocompatibility.

In terms of flowability and reactivity, the average grain size (D50) of the hydraulic cement may be maintained not greater than 3 micron. The hydraulic cement may be included at 15 to 55 wt % with respect to the entire composition.

Further, in the composition according to the disclosure, calcium chloride having hygroscopic and deliquescent properties may also be added to the hydraulic cement to enhance the hygroscopicity of the paste and enable fast and secure hardening, while maintaining biocompatibility and enhancing sealing properties. In this case, the calcium chloride may be included at 1.5 to 5.5 wt % with respect to the entire composition.

Furthermore, in the composition according to the disclosure, an active silica material may be included in Portland cement to employ Pozzolan cement, which uses water for crystallization in a hydration process as in the chemical formula below. (In connection with the composition of Pozzolan cement, reference may be made to Korean Registered Patent Publication No. 1000402, which is incorporated herein in its entirety.)

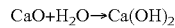

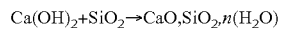

When Pozzolan cement is employed, the composition according to the disclosure may be obtained without the addition of calcium chloride, with the assistance of the crystallization water produced according to the above chemical formula.

2) Non-Aqueous Liquid

The composition according to the disclosure may comprise non-aqueous liquid having hygroscopic properties to convert the hydraulic cement into the form of paste.

The non-aqueous liquid may include substantially no water, which would react with the hydraulic cement to produce a hydration reaction, or may include minimal moisture that does not cause hardening. In the non-aqueous liquid, water may be included at 3 wt % or less with respect to the non-aqueous liquid. The non-aqueous liquid may be required to have properties such as biocompatibility, preservation stability, hygroscopicity, surface activity, water miscibility, and quick absorption into a human body.

The above non-aqueous liquid may comprise at least one selected from a group consisting of N-methyl-2-pyrrolidone (NMP), polyoxyethylene sorbitan monolaurate, dimethyl isosorbide, diethylene glycol dimethyl ether (diglyme) or diethylene glycol monoethyl ether (carbitol cellosolve), and butylene glycol, and may comprise NMP.

The non-aqueous liquid may be included at 15 to 35 wt % with respect to the entire composition. The content less than 15 wt % makes it difficult to ensure proper flowability, while the content greater than 35 wt % makes the flowability excessively high and hinders the hydration reaction.

3) Radiopaque Material

The composition according to the disclosure may comprise a radiopaque material for easy reading, e.g., at least one selected from a group consisting of barium sulfate, zirconium oxide, bismuth oxide, tantalum oxide, and calcium tungstate, and may employ bismuth oxide or zirconium oxide to ensure high radiopacity and biocompatibility.

The radiopaque material may be included at 20 to 55 wt % with respect to the entire composition.

4) Hygroscopic Clay

The combination of the hygroscopic cement and the non-aqueous hygroscopic liquid as described above may be somewhat inadequate to ensure that a hardening process is carried out even within an extremely dry root canal. Thus, hygroscopic clay may be additionally included to achieve higher hygroscopicity and satisfy other requirements of the root canal filler, e.g., sufficient flowability, manipulability, and ultrasonic transmissibility. (However, the hygroscopic clay may not be a component that should be necessarily included.)

The hygroscopic clay may comprise at least one selected from a group consisting of bentonite, smectite, and swelling synthetic clay minerals, and may comprise bentonite.

Since Bentonite consists of various types of natural clay, it may achieve viscosity stability and structure formation over a wide temperature range, may enhance resistance to sagging or exfoliation, may act as a retarder to improve open time of Portland cement, and may have an antibacterial effect due to its resistance to bacteria or enzymes.

The hygroscopic clay may be included at 1 to 10 wt % with respect to the entire composition.

5) Hygroscopic Viscosity Enhancing Agent

In order to impart proper viscosity to the non-aqueous liquid, the composition according to the disclosure may further comprise at least one hygroscopic viscosity enhancing agent selected from a group consisting of hydroxyethyl cellulose, hydroxypropyl methylcellulose, carboxymethyl cellulose, polyvinyl alcohol, and polyvinylpyrrolidone.

The viscosity enhancing agent may prevent separation of the paste, may preserve moisture, may increase manipulability, may increase cohesion, may act as a surfactant to facilitate deep penetration of the root canal filling material, and may enable the surface of the paste to be maintained smooth. Further, it has high resistance to bacterial molds and has excellent storage stability.

The viscosity enhancing agent may be included at 0.1 to 1 wt % with respect to the entire composition.

Preparation examples of the disclosure will be described below in more detail.

Preparation Examples 1 to 3

100 parts by weight of Portland cement, 20 parts by weight of bentonite, 10 parts by weight of calcium chloride, and 100 parts by weight of zirconium oxide were mixed to prepare powder, which was then mixed with NMP containing 2 wt % of methylcellulose, NMP containing 7 wt % of polyvinyl alcohol, and NMP containing 7 wt % of polyvinylpyrrolidone, respectively, to prepare single paste type hydraulic dental filling compositions.

Each of the pastes was stored in a syringe and cut off from air. When they were exposed out of the syringes for use thereof, all of them absorbed moisture from atmosphere with the humidity of 50% and hardened within two days.

As such, it was seen that the composition according to the disclosure securely hardens in a humid environment.

Preparation Examples 4 to 6

200 parts by weight of EndocemZR (a product in which Pozzolan cement and zirconium oxide are mixed at a 1:1 ratio) and 20 parts by weight of bentonite were mixed to prepare powder, which was then mixed with NMP containing 2 wt % of methylcellulose, NMP containing 7 wt % of polyvinyl alcohol, and NMP containing 7 wt % of polyvinylpyrrolidone, respectively, to prepare single paste type hydraulic dental filling compositions.

Each of the pastes was stored in a syringe and cut off from air. When they were exposed out of the syringes for use thereof, all of them absorbed moisture from atmosphere with the humidity of 50% and hardened within two days.

As such, it was seen that the composition according to the disclosure securely hardens in a humid environment.

The filling composition prepared according to Preparation Example 2 among the above examples was employed in conducting the exemplary tests below.

Test Example 1: Solubility Test

According to the test methods specified in Section 5.6 of ISO 6876:2012(E), the solubility of the filling composition according to the disclosure was measured as follows:

First, 2 g of the filling composition mixed with 0.02 ml of water was filled in a mold with the diameter of 20±1 mm and the width of 1.5±0.1 mm, and kept in an oven at 37±1° C. for 150% or greater of hardening time. Then the sample was taken out from the mold and weighed. Two pieces of the sample were put in a dish and 50±1 ml of distilled water was poured, and then the dish was kept in the oven at 37±1° C. for 24 hours. After the dish was taken out, the distilled water was percolated with filter paper and then poured into a pre-weighed beaker. About 5 ml of distilled water was put in the dish that contained the sample to wash it, and then was percolated. The beaker was put in the oven at 110±2° C. to evaporate the distilled water, and then cooled to room temperature and weighed. The difference between the weight of the beaker and that of the beaker from which the distilled water was evaporated was recorded and regarded as the amount of the dissolved sample, which was converted into a percentage and regarded as the solubility. The result is shown in TABLE 1.

TABLE 1

| Weight of sample | 1.0416 g | 1.0786 g | 1.0400 g | 1.0741 g |
|---|---|---|---|---|
| Weight of beaker | | 60.5494 g | | 59.5955 g |
| Weight of beaker from which solution was evaporated | | 60.5704 g | | 59.6112 g |
| Weight of dissolved sample | | 0.0210 g | | 0.0157 g |
| Solubility | | 1.0% | | 0.7% |
| Average | | 0.85% (SD 0.21%, CV 24.96%) | | |

Test Example 2: Size Change Test

According to the test methods specified in Section 7.6 of ISO 6876:2001(E), the change in the size of the filling composition according to the disclosure was measured as follows:

First, 2 g of the filling composition mixed with 0.02 ml of water was filled in a mold with the inner diameter of 6 mm and the height of 12 mm, and the top and bottom thereof were covered with a film and a glass plate. The mold and the sample were kept in an oven at 37±1° C. during hardening, and hardening time was measured. When the sample was hardened, the top and bottom thereof were abraded together with the mold to flatten them, and then the sample was removed from the mold. The length of the sample was measured and then the sample was kept in distilled water at 37±1° C. for thirty days. Thereafter, the length of the sample, the rate of change (%) from the original length, and the average thereof were measured. The result is shown in TABLE 2.

TABLE 2

| Hardening time | 11.62 min | 10.03 min | 11.42 min |
|---|---|---|---|
| Average | 11.023 min (SD 0.866 min, CV 7.86%) | | |
| Length (Day 0) | 11.98 mm | 11.59 mm | 11.19 mm |
| Length (Day 30) | 12.49 mm | 12.06 mm | 11.62 mm |
| Difference | 0.51 mm | 0.47 mm | 0.43 mm |
| Rate of change | 4.26% | 4.06% | 3.84% |
| Average | 4.053% | | |

Test Example 3: Film Thickness Test

According to the test methods specified in Section 5.5 of ISO 6876:2012(E), the film thickness of the filling composition according to the disclosure was measured as follows:

First, three pairs of glass plates were prepared, and the thickness of two glass plates was measured with 1 μm accuracy using electronic inside calipers. 0.05 ml of the composition was taken and put on the center of a glass plate. After three minutes, another glass plate was covered thereon and a weight of 150 N was applied. At this time, it was seen that the sample was completely filled between the glass plates. After ten minutes, the weight was removed and the thickness of the glass plates was measured. The difference in the measured thickness of the glass plates was calculated and regarded as the film thickness. The result is shown in TABLE 3.

TABLE 3

| Thickness of glass plates | 5,694 μm | 5,553 μm | 5,597 μm |
|---|---|---|---|
| Thickness of glass plates filled with sample | 5,719 μm | 5,568 μm | 5,613 μm |
| Film thickness | 25 μm | 15 μm | 16 μm |
| Average | 18.7 μm (SD 5.5 μm, CV 29.50%) | | |

Test Example 4: pH Test (1) pH measurement of original paste: After the weight of the composition was measured, the composition was immersed in distilled water weighing tenfold the weight, and then pH was measured.

(2) pH measurement right after hardening: 2 g of the composition mixed with 0.02 ml of distilled water was filled in a mold with the diameter of 15±0.1 mm and the depth of 1.0±0.1 mm, and was sufficiently hardened. Then, it was removed from the mold and pH was measured as in (1).

(3) pH measurement after one day from hardening: The test liquid of (2) was kept in a constant-temperature oven at 37±1° C., and then pH of the test liquid was measured after one day from the hardening.

(4) pH measurement after seven days from hardening: After the measurement in (3) was finished, the test liquid of (2) was kept in the constant-temperature oven at 37±1° C., and then pH of the test liquid was measured after seven days from the hardening.

pHs of the three test liquids of (2) to (4) were averaged, and the result is shown in TABLE 4 and FIG. 1.

TABLE 4

| | | Test liquid (2) | Test liquid (3) | Test liquid (4) |
|---|---|---|---|---|
| Paste | pH | 11.22 | 11.47 | 11.56 |
| | Average | 11.417 (SD 0.176, CV 1.54%) | | |
| Right after hardening | pH | 10.61 | 10.58 | 10.55 |
| | Average | 10.580 (SD 0.030, CV 0.28%) | | |
| 1 day after hardening | pH | 11.94 | 11.88 | 11.90 |
| | Average | 11.907 (SD 0.031, CV 0.26%) | | |
| 7 days after hardening | pH | 11.74 | 11.76 | 11.81 |
| | Average | 11.770 (SD 0.036, CV 0.31%) | | |

Although the present disclosure has been described in terms of specific items such as detailed elements as well as the limited embodiments and the drawings, they are only provided to help more general understanding of the disclosure, and the present disclosure is not limited to the above embodiments. It will be appreciated by those skilled in the art to which the present disclosure pertains that various modifications and changes may be made from the above description.

Therefore, the spirit of the present disclosure shall not be limited to the above-described embodiments, and the entire scope of the appended claims and their equivalents will fall within the scope and spirit of the disclosure.

What is claimed is:

1. A single paste type hydraulic dental filling composition, comprising:
   hydraulic cement;
   non-aqueous liquid having hygroscopic properties;
   a radiopaque material; and
   hygroscopic clay.

2. The single paste type hydraulic dental filling composition as claimed in claim 1, wherein the content of the hydraulic cement is 15 to 55 wt % with respect to the entire composition, the content of the non-aqueous liquid is 15 to 35 wt % with respect to the entire composition, and the content of the radiopaque material is 20 to 55 wt % with respect to the entire composition.

3. The single paste type hydraulic dental filling composition as claimed in claim 1, wherein an average grain size (D50) of the hydraulic cement is 3 micron or less.

4. The single paste type hydraulic dental filling composition as claimed in claim 1, wherein the hydraulic cement comprises calcium oxide or calcium hydroxide as an active component.

5. The single paste type hydraulic dental filling composition as claimed in claim 1, wherein the hydraulic cement comprises Portland cement or Pozzolan cement.

6. The single paste type hydraulic dental filling composition as claimed in claim 1, wherein the non-aqueous liquid comprises at least one selected from a group consisting of N-methyl-2-pyrrolidone (NMP), polyoxyethylene sorbitan monolaurate, dimethyl isosorbide, diethylene glycol dimethyl ether (diglyme), diethylene glycol monoethyl ether (carbitol cellosolve), and butylene glycol.

7. The single paste type hydraulic dental filling composition as claimed in claim 1, wherein the radiopaque material comprises at least one selected from a group consisting of barium sulfate, zirconium oxide, bismuth oxide, tantalum oxide, and calcium tungstate.

8. The single paste type hydraulic dental filling composition as claimed in claim 1, wherein the content of the hygroscopic clay is 1 to 10 wt % with respect to the entire composition.

9. The single paste type hydraulic dental filling composition as claimed in claim 1, wherein the hygroscopic clay comprises at least one selected from a group consisting of bentonite, smectite, and swelling synthetic clay minerals.

10. The single paste type hydraulic dental filling composition as claimed in claim 1, wherein the non-aqueous liquid comprises a hygroscopic viscosity enhancing agent.

11. The single paste type hydraulic dental filling composition as claimed in claim 10, wherein the content of the hygroscopic viscosity enhancing agent is 0.1 to 1 wt % with respect to the entire composition.

12. The single paste type hydraulic dental filling composition as claimed in claim 10, wherein the hygroscopic viscosity enhancing agent comprises at least one selected from a group consisting of hydroxyethyl cellulose, hydroxypropyl methylcellulose, carboxymethyl cellulose, polyvinyl alcohol, and polyvinylpyrrolidone.

13. The single paste type hydraulic dental filling composition as claimed in claim 1, wherein calcium chloride having hygroscopic and deliquescent properties is added to the hydraulic cement.

14. The single paste type hydraulic dental filling composition as claimed in claim 13, wherein the content of the calcium chloride is 1.5 to 5.5 wt % with respect to the entire composition.

* * * * *